United States Patent [19]

Bowlds

[11] Patent Number: 5,422,485
[45] Date of Patent: Jun. 6, 1995

[54] INFRARED BREATH ANALYZER WITH CALIBRATION PROVISIONS AND RELATED METHOD

[75] Inventor: Harvey F. Bowlds, Owensboro, Ky.

[73] Assignee: CMI, Inc., Owensboro, Ky.

[21] Appl. No.: 89,216

[22] Filed: Jul. 9, 1993

[51] Int. Cl.$^6$ .............. G01D 18/00; G01N 21/61; G01N 37/00
[52] U.S. Cl. .................. 250/343; 250/252.1
[58] Field of Search .......... 250/252.1 A, 343

[56] References Cited

U.S. PATENT DOCUMENTS

| 3,825,756 | 7/1974 | Weiss | 250/343 |
| 4,268,751 | 5/1981 | Fritzlen et al. | 250/343 |
| 4,692,621 | 9/1987 | Passaro et al. | 250/343 |

FOREIGN PATENT DOCUMENTS

| 3150013 | 6/1983 | Germany | 250/252.1 A |
| 61-215949 | 9/1986 | Japan | 250/252.1 A |
| 1-297532 | 11/1989 | Japan | 250/252.1 A |

Primary Examiner—Constantine Hannaher
Attorney, Agent, or Firm—King & Schickli

[57] ABSTRACT

A calibration device, method and apparatus is provided for checking calibration of a breath alcohol measuring instrument. A silicon wafer with an anti-reflective silicon monoxide coating on both sides is used to attenuate the infrared radiation in the range of 3.35 to 3.80 microns wavelength in a manner to simulate the attenuation caused by a breath sample containing 0.10 BrAC. A comparison of the signal generated by the attenuation at a wavelength of approximately 3.48 microns is made to the baseline signal obtained before placing the calibration disk in the IR beam path and accurately simulates the breath sample. The related breath alcohol measuring method and apparatus provides for the positioning of the composite disk in the path between the infrared source and receiver. A computer compares the signals and performs the calibration check, as well as the actual BrAC analysis.

11 Claims, 2 Drawing Sheets

INFRARED BREATH ANALYZER WITH CALIBRATION PROVISIONS AND RELATED METHOD

TECHNICAL FIELD

The present invention relates to breath analyzing instruments utilizing infrared radiation to measure the amount of alcohol in a breath sample, and specifically, an improvement in calibration of such instruments.

BACKGROUND OF THE INVENTION

Instruments measuring the alcohol content in a breath sample have become a common and effective tool utilized by business human resource personnel, government officials, and law enforcement agencies to evaluate whether a person is under the influence of alcohol. The statutory offense of driving-under-the-influence is defined in most states as operating a vehicle while having a blood alcohol content greater than 0.10 percent. A typical breath alcohol measuring instrument utilizes infrared radiation (IR) to calculate the content of ethyl alcohol (ethanol) in a breath sample, from which blood alcohol content is readily calculable.

Such an instrument utilizing infrared radiation includes a sample cell forming a chamber that receives and retains a breath sample. A person being tested blows a breath sample into the chamber and infrared radiation attenuation at at least two different wavelengths is monitored during the residence time of the breath sample in the chamber. The first wavelength is selected to be attenuated by the ethanol while the second wavelength is not attenuated. The signal representing the second wavelength is compared to a signal representing a baseline value stored in the system's computer, and is used primarily to stabilize the instrument to prevent long term drift due to aging of components, such as the inevitable weakening of the IR source. The amount of the attenuation at the first wavelength is calculated by the computer by comparing the difference between the signals representing the radiation received before the breath sample, to that received when the sample is present in the chamber.

Precise and reliable calibration of infrared breath alcohol measuring instruments is very important because even small errors in the measured attenuation can cause relatively large errors in the alcohol content determined by the computer. To avoid improper arrest and charges, including for driving-under-the-influence, and to maintain the credibility of the instruments and alcohol readings taken thereby, reliable and precise calibration is required.

The most common calibration check technique for infrared breath alcohol measuring instruments is the "wet" method. Briefly in this prior art method, a gas/vapor of known alcohol content is introduced into the sample chamber, and infrared radiation is passed therethrough. The attenuation induced by the vapor is measured and the alcohol content in the vapor is determined by the computer. The determined alcohol content is then compared to the known alcohol content (usually 0.10%) of the calibration gas. In the unlikely event that the determined alcohol content and the known alcohol content differs, appropriate adjustment or other remedial action is taken, and the instrument is tested again until the two readings match.

The "wet" method of checking calibration possesses significant drawbacks that have provided impetus for a search for an improved calibration check means and method. One specific disadvantage is that a sufficient supply of a calibration mixture of water and ethanol must be maintained with the instrument, even in the field applications. Typically this means hauling around a bulky tank of water/ethanol with the instrument. Another disadvantage is that the water/alcohol mixture must be maintained at a suitable, relatively high temperature to form the vapor prior to introduction into the instrument. This adds a need for providing bulky electric heaters, especially in colder climates, as well as limiting use to locations where an electric power source is available.

A relatively recent innovation in calibrating breath alcohol measuring instruments has been the introduction of solid calibration plates to replace the wet method of calibration. A solid calibration plate is placed in the path of infrared radiation and simulates a breath sample of the predefined alcohol content by causing similar attenuation of the radiation. Solid calibration plates disclosed in the prior art include various partially IR transparent substrates allowing the correct amount of infrared radiation to pass therethrough. One example of such a device is a comb mask, as disclosed in U.S. Pat. No. 3,562,524.

These known prior art solid calibration plates, in spite of the decided advantages over the wet method, are not widely in use, mainly because of questionable reliability. Also, some substrates previously proposed for use have been problematic due to lack of durability. This is a particular problem in mobile installations. Fine scratches or smudges on the substrates, whether formed on an interrupted or solid body, significantly affect the attenuation of infrared radiation, making them unreliable for calibration, especially when they are handled by hand. This condition can sometimes be hard to detect, especially by an inexperienced operator. If the defects are not immediately detected, an improper conclusion is often reached that the instrument is in need of adjustment or repair, instead of the calibration plate being defective.

Thus, as demonstrated by these disadvantages, there is a need identified for an easily transported, yet reliable means for checking calibration of a breath alcohol measuring instrument.

SUMMARY OF THE INVENTION

Accordingly, it is a primary object of the present invention to provide a calibration check device, and related method, for verifying calibration of a breath alcohol measuring instrument including a simple composite substrate and coatings, so as to overcome the limitations of the prior art.

Another object of the invention is to provide a breath alcohol measuring instrument that is easily transportable, and includes a built-in and light weight calibration check device including robotic handling, so that the instrument can be reliably and efficiently verified in the field.

It is yet another object of the present invention to provide a breath alcohol instrument/method utilizing infrared radiation that incorporates a simple and durable substrate with special coatings that simulates a breath sample containing a predetermined percent of alcohol.

It is another object of the present invention to provide a breath alcohol measuring device and related method and instrument incorporating a composite disk for verifying calibration, as well as making provision for properly positioning the composite disk in the path of infrared radiation without being touched by human hands.

To achieve the foregoing and other objects, an improved calibration device is provided for checking calibration of a breath alcohol (BrAC) measuring instrument wherein a beam of infrared radiation (IR) is passed through a breath sample to determine alcohol content. The calibration device comprises a substrate coated with an anti-reflective coating that uniquely attenuates infrared radiation so as to accurately simulate a breath sample containing a defined percent of alcohol.

In the preferred embodiment, the calibration device includes a composite disk with the anti-reflective (AR) coating on both sides; the coating preferably comprising thin layers of silicon monoxide (SiO). The substrate is preferably a silicon (Si) wafer having a thickness of approximately 2.5 millimeters (mm), and the AR coatings are selected to be approximately 5940 Å units in thickness. Infrared radiation (IR) with wavelengths between 3.35 and 3.80 microns, and more specifically wavelengths of 3.48 and 3.80 microns, are used in the comparative testing to provide the percent alcohol reading. This particular composite disk is very reliable in duplicating a 0.10 percent ethanol calibration reading.

A related method is provided for calibrating a breath alcohol measuring instrument having a cell with a sample chamber, an infrared radiation source, an IR receiver, a radiation path therebetween and a computer. The first step is providing the composite disk for insertion in the radiation path for comparative attenuation of the infrared radiation having wavelengths between 3.35 and 3.80 microns that simulates a breath sample containing the predetermined 0.10% BrAC (or some other predetermined value). The composite disk provided by the present invention includes the substrate coated with the anti-reflective coating, as identified above.

Upon initial set up of the instrument, the known or equivalent alcohol value (usually 0.10% BrAC) for the disk is stored in the computer memory. This equivalent value, defined as the target alcohol content in a breath sample, provides the "known" value that is subsequently used to verify proper calibration of the instrument. The method further includes the step of purging the sample chamber of the instrument with fresh air and baseline values are established. It is very important to remove any remnants of a previous breath sample before this test procedure is initiated. Next, the disk is positioned in the radiation path, and infrared radiation sent along the radiation path and through the disk. The IR is then directed to the receiver. The attenuation is computed, and the apparent alcohol content thus denoted, and is compared to the known alcohol concentration value stored in the computer to verify proper calibration.

In a further aspect of the present invention, and in accordance with its objects and purposes, a breath alcohol measuring instrument is provided incorporating a composite calibration disk. The instrument includes a sealed cell having a sample chamber for receiving and retaining a breath sample. A pump initially fills the chamber with fresh air. An infrared radiation source, an IR receiver and a radiation path are provided; the IR path being defined at least partially by the chamber. Selective filters are used for filtering the infrared radiation so that two (or more) specific IR wavelengths, namely, at least approximately 3.48 and 3.80 microns, are received by the IR receiver. The 3.80 micron wavelength, or second wavelength as referred to above, is used by the computer to periodically monitor the overall performance of the instrument's components, and in response adjust and stabilize the instrument. The amount of adjustment, if any is determined by comparison to a signal representing the instrument's overall baseline value, as stored in the computer. This is the feature of the instrument that prevents drift in the instrument's calibration due to such naturally occurring factors as dimming of the IR source.

The calibration disk includes the unique coated substrate and is placed in the IR path to provide a signal that emulates a breath sample containing a defined percent of alcohol; that is, an attenuated signal representing the 3.48 micron wavelength, which in turn, is equivalent to 0.10 BrAC. The computer compares the actual signal received when the disk is in the path to the signal representing the baseline value without the disk, as stored in the computer memory. As a result, the appropriate attenuation at the IR receiver is measured, and when there is a match with the known value, the calibration of the instrument is checked. That is, when the apparent alcohol content between the source and receiver provided by the calibration disk does not deviate from the known value, the precise calibration of the instrument is proven.

A robotic handler is provided to selectively shift the composite disk into and out of the IR beam path so that potential damage to the disk is obviated.

A digital display denotes the simulated percentage of alcohol content. In the unlikely event that the reading during the calibration check does not match, the instrument provides a signal that adjustment or repair is necessary and/or locks out further use until this is done.

In a further and more detailed aspect of the present invention, the robotic handler for positioning the composite disk into/out of the light path includes a stepper motor, the shaft of which carries an oscillating support arm and on which the composite disk is mounted. A switch triggers operation of the stepper motor to position the disk into the radiation path for calibration.

In a further specific aspect of the present invention, an environmentally controlled housing is constructed around at least the portion of the instrument including the composite disk. This is important because it eliminates the potential for fluctuations of the attenuation of the IR beam caused by changes in the temperature or humidity of the disk.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

FIG. 3 is a cross-sectional view of the composite disk, specifically illustrating the silicon substrate and the silicon monoxide coatings.

DETAILED DESCRIPTION OF THE INVENTION

Figure 1:
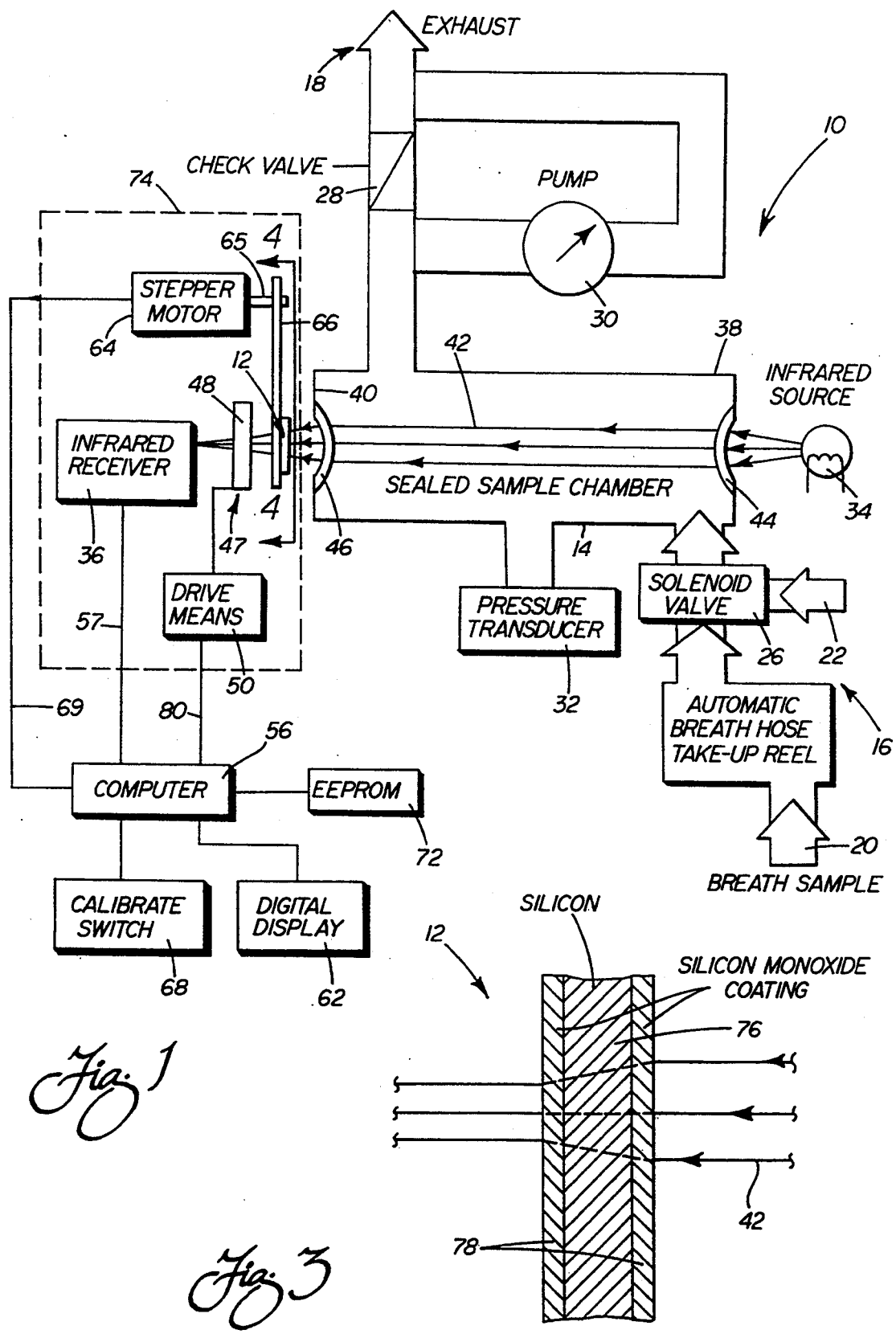
FIG. 1 is a schematic diagram of an infrared breath alcohol measuring instrument incorporating a composite calibration disk that includes a substrate and anti-reflective coatings, and a robotic handler for positioning the disk in the infrared radiation path.

Reference is now made to FIG. 1, wherein a breath alcohol measuring instrument 10 is schematically illustrated and incorporates a composite calibration disk 12 of the present invention. The instrument 10 is constructed to include a cell 14 forming a sealed sample chamber; and with an inlet assembly 16 for receiving a breath sample, and an exhaust passage 18 for releasing the vapor/gas. The inlet assembly 16 includes a breath sample port 20, which may include an automatic breath hose take-up reel, and an external simulator port 22. If desired, either a dry gas or "wet" calibration supply (not shown) may be connected to the port 22 for allowing a two-phase calibration system or double checking from time to time, if desired. A solenoid valve 26 is operable to switch between the breath sample port 20 and the external simulator port 22. The exhaust passage 18 includes a check valve 28 through which excess pressure gas/vapor is allowed to escape from the sample chamber of the cell 14. Gas/vapor is actively purged from the chamber 14 by a pump 30 in parallel with the check valve 28. The pump 30 is specifically used to purge the cell 14 in preparation for calibration or to test a breath sample. A pressure transducer 32 monitors the pressure within the cell 14 and determines the sufficiency of a breath sample contained in the chamber for testing.

An infrared radiation source 34 and IR receiver 36 are provided adjacent opposite ends 38, 40 of the sample cell 14, such that a radiation path 42 is defined through the sample chamber 14. Lenses 44, 46 mounted at the respective ends 38, 40 of the sample chamber 14 focus the infrared radiation propagating between the source 34 and receiver 36.

Figure 2:
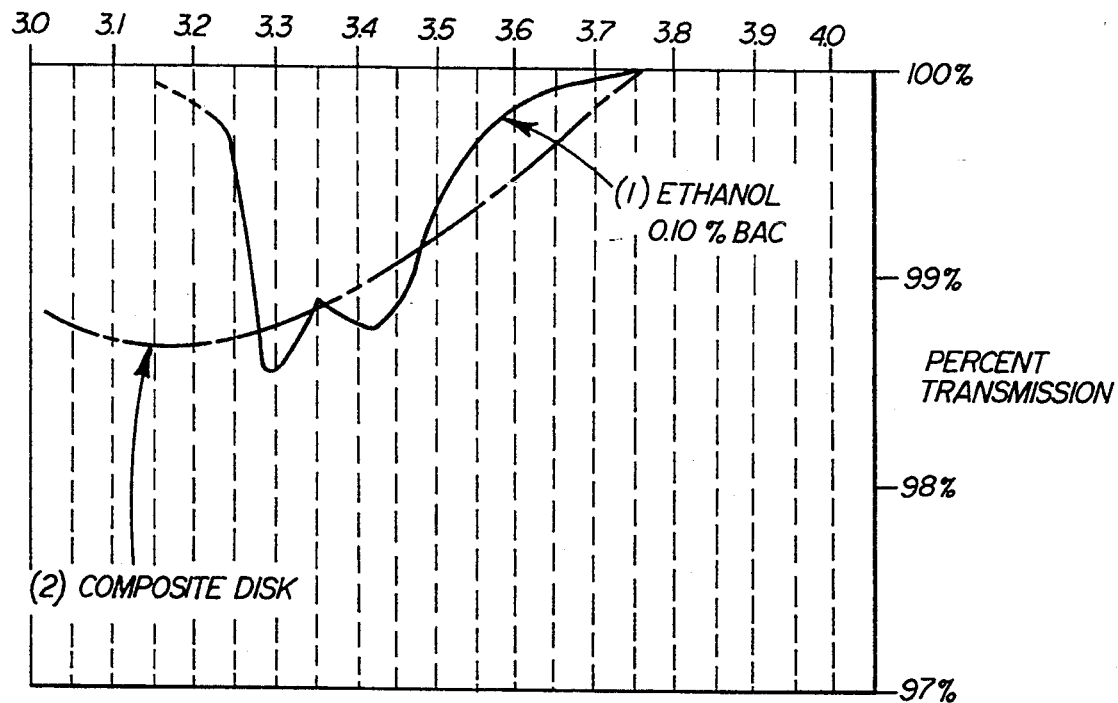
FIG. 2 is a graph showing the attenuation curves of infrared radiation over the range of wavelengths 3.30 to 3.80 microns caused by (1) a breath sample containing 0.10 percent ethanol, and (2) the composite disk of the present invention for calibration of the instrument of FIG. 1.

Filter assembly 47 is provided to restrict the infrared radiation received at the IR receiver to at least two bandwidths within a relatively narrow range that is uniquely responsive to the presence of ethanol; namely, the range of approximately 3.35–3.8 microns (see FIG. 2). A filter wheel 48 is rotatably driven by drive means 50 (see action arrow R in FIG. 4). The wheel 48 is driven such that spaced apertures 52, 54 with diverse filters 53, 55, respectively, are alternately positioned in and out of the radiation path 42, whereby only infrared radiation having the two selected, specific wavelengths are allowed to reach the receiver 36. Specifically, the filter 53 may open the path 42 to allow only infrared radiation with a 3.48 microns wavelength to pass through. This wavelength is strongly attenuated by the presence of ethanol in the chamber, or by the disk 12 that simulates ethanol. The 3.80 microns IR wavelength on the other hand, is not significantly attenuated by either an ethanol breath sample or the disk 12. The selection of these two wavelengths are ideally suited for proper basic calibration, and then checking the calibration, as well as detection at 0.10 percent BrAC (note substantially 100% transmittance and coincidence of ethanol/composite disk curves (1 & 2) in FIG. 2). In other words, at the 3.48 microns first wavelength infrared radiation attenuation is caused by the disk 12, or by a 0.10 percent alcohol sample to substantially the identical degree; whereas, at the 3.80 microns second wavelength, there is no attenuation by either.

According to the particular characteristics of the disk 12 of the present invention, after the sample chamber is purged with fresh air, a baseline reading is taken at both wavelengths and stored in computer 56. The composite disk 12 is then placed in the IR path 42, which causes attenuation properties that substantially follow the actual ethanol curve (1), as illustrated by the overlaid composite disk curve (2) in FIG. 2. Advantageously, the instrument 10, in response to positioning of the filters 53, 55 in the IR path 42 automatically checks to see in effect if there is a difference or delta radiation from the baseline values previously obtained at the two wavelengths. If the reading at the second wavelength indicates drift, the instrument 10 is immediately adjusted to compensate for the problem. The composite disk 12 actually simulates the presence of alcohol, so that at the first wavelength the final calibration check is made. In other words, when a 0.10 readout appears with the composite disk 12 in the path 42, the operator is assured of getting an accurate reading when the immediately following actual breath sample is taken.

In making the calculation for either calibration or breath analysis, the computer 56 receives the two sequential signals from the receiver 36 over line 57 representing the radiation received at the 3.48 microns reference wavelength (attenuated signal) and the 3.80 microns wavelength (non-attenuated signal). Assuming the instrument is stabilized by a favorable comparison at the 3.80 micron wavelength, and the comparison of the reference attenuated signal to the reference baseline signal is favorable, calibration to 0.10% BrAC in a highly accurate manner, is assured. Then when an actual breath sample is present, the instrument's reading similarly represents the actual BrAC percentage, that is, 0.10% BrAC, lesser or greater, in the actual testing mode.

Figure 4:
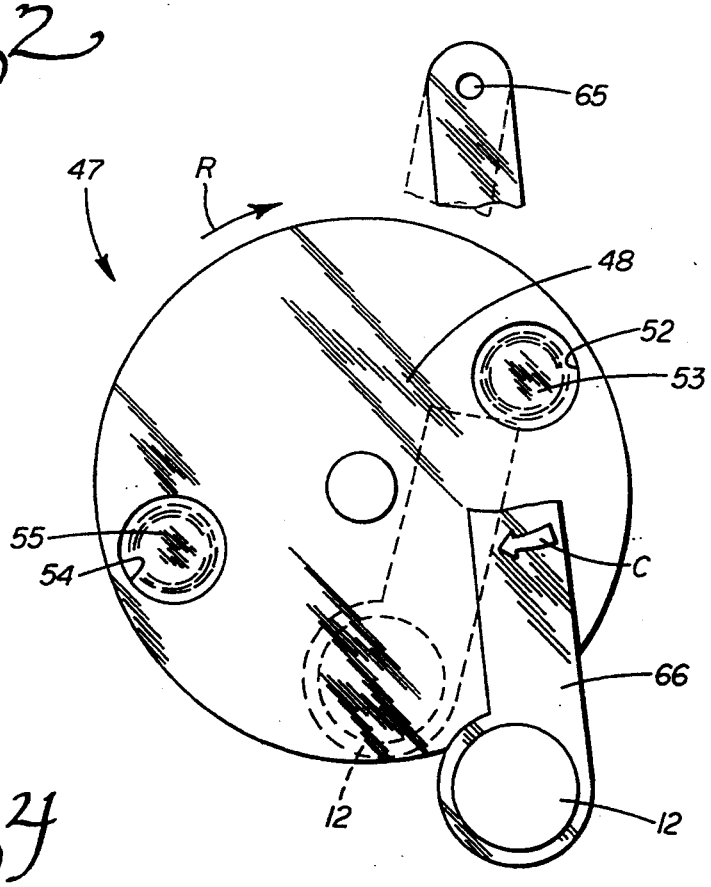
FIG. 4 is a front view taken along line 4—4 of FIG. 1 illustrating the relative positioning of the filter wheel, composite calibration disk and support arm during normal operation of the instrument (full-line) and during the calibration check mode (dotted line outline).

As indicated above, the composite disk 12 is shown in FIG. 1 positioned within the breath alcohol measuring instrument 10 (see also FIG. 4, for more detail). A robotic handler positions the composite disk 12 within the light path 42. The preferred embodiment includes a stepper motor 64 with shaft 65 for supporting oscillating mounting arm 66, which in turn carries the composite disk 12. A switch 68 triggers the stepper motor 64 to swing the mounting arm 66 so that the disk 12 is positioned in the path 42 for the calibration check mode (see direction arrow C in FIG. 3). The operation of the stepper motor is controlled, as well as being synchronized with the computer 56 by signals over line 69.

To check for proper calibration, the computer 56 compares the apparent alcohol content resulting from the radiation passing through the composite disk 12 to an equivalent alcohol concentration value stored in computer memory EEPROM 72. The equivalent alcohol concentration value is thus characteristic of or matched to the composite disk 12. It is defined upon initial set up of the instrument 10, and during subsequent wet-bath full service instrument recalibrations.

In accordance with an important aspect of the invention, the preferred embodiment of the composite disk 12 comprises a 2.5 mm thick silicon wafer, designated by the reference numeral 76, with a 5940 Å thick coating 78 of silicon monoxide on each side (see FIG. 3). This particular construction is proven to be rugged so as not to be adversely affected by vibration or jolts, as particularly may be experienced in mobile installations. Furthermore, the material of the disk 12 is stable and does not deteriorate or change IR attenuation characteristics or value over time. If the instrument 10 is to be operated under widely varying or extreme temperatures and/or humidity conditions, an environmentally controlled housing 74 may be provided to isolate the composite disk 12.

In accordance with the broader aspects of the present invention, the substrate 76 of the disk 12 can be fabricated of other materials so long as the desired attenuation characteristics of the IR beam are attained. It is contemplated that other dielectric materials, such as quartz, can be identified to serve as the substrate to provide the appropriate basic radiation attenuation properties. The criteria for selection of such a material for the substrate 76 centers on the IR translucent properties, and may be determined empirically, and refined by trial and error. The objective is to provide the properties to approach the curve of the present preferred embodiment of the composite disk 12, as depicted by the curve (2) over the range of 3.35–3.80 microns (see FIG. 2). Also, of importance, is the use of the appropriate anti-reflective coatings 78 that enhance the attenuation properties, and as have been discovered to provide an important aspect of closely matching the actual ethanol curve (1) of FIG. 2.

For selection of the anti-reflective coatings 78 for the particular disk 12, empirical and trial and error procedures are also appropriate. Measuring the attenuation properties of the substrate 76 and the coatings 78, combining the figures, factoring in the reduction in IR beam reflection at the coating/air interface and then simply testing the composite disk is the proven approach.

For example, successful matching of a selected material for the substrate 76 with the coatings 78 to provide the curve (2) for calibration in the infrared instrument 10 may include the selection of magnesium fluoride, zinc sulfide and/or several rare earth oxides. With any of the coatings, thin films are applied to one or both sides of the substrate 76 and a selected number of layers can be provided in any given instance for controlling or modifying the IR reflection and transmission qualities in order to attain the desired attenuation. Furthermore, different optical coatings applied in layers to make up the coatings 78 on the substrate 76 can be used to refine the curve (2) in order to attain as close of coincidence as possible with the attenuation curve (1) represented by ethanol (see FIG. 2).

In practicing the method of the present invention for calibrating a breath alcohol measuring instrument 10 with the infrared source 34, the receiver 36, the radiation path 42 through the cell 14 and the computer 56 to process the signals, the key step is to purge the chamber 38 with fresh air and pass the IR beam through the composite disk 12 including the substrate 76 and matching anti-reflective coatings 78, and the filters 53, 55 for a simulated BrAC test. The composite disk 12 is selected, as set forth above to attenuate the infrared radiation of wavelengths of approximately 3.35–3.80 microns. This range is, of course, inclusive of the first selected wavelength 3.48 microns, which exhibits the greatest attenuation properties matching that of 0.10 BrAC. The second selected wavelength 3.80 microns, which exhibits no attenuation, is also included. After a successful comparative analysis in the computer 56 of the signals representing both the first and second wavelengths with their baseline values, and then the calibration check is made as described, the accurate calibration of instrument 10 is assured.

To further explain, for the important calibration check, the disk 12 is positioned in the radiation path 42 so that the attenuated IR beam is received by the infrared receiver 36. Simulated attenuation is thus measured, and comparison of this signal to the previously stored signal provides the desired calibration check. In other words, this step involves comparing the apparent alcohol content to the known or equivalent alcohol concentration value in the computer memory from the initial set-up or a previous full service calibration, thereby verifying the proper calibration of the instrument 10 at the time of use in the field.

Preferably in the calibration method, as indicated above, the baseline value is established by observing and/or registering the IR intensity at the first wavelength while the sample chamber contains fresh air only, and with the calibration disk out of the IR beam. From this baseline, the first wavelength is differentiated so that the result provides a signal indicative of the amount of breath alcohol in the sample during the actual testing.

In accordance with another aspect of the present invention, the breath alcohol measuring instrument 10 includes a sealed sample chamber within the cell 14, means 30 for purging the chamber with fresh air, an infrared radiation source 34 and receiver 36 defining a radiation path for the IR beam, filtering means 47 to provide at least the two specific wavelengths to the receiver, a first wavelength being attenuated by breath alcohol and the second wavelength not being attenuated, a composite disk 12 for causing strong attenuation of the IR beam at approximately the first wavelength and substantially none at the second, and computer means for processing the information for stabilizing and calibrating the instrument.

The information for comparison during the calibration check is an equivalent alcohol concentration value provided during a full service calibration, such as upon initial set up or a regular follow-up servicing of the instrument. The computer 56 includes means not only for comparing the concentration value with the apparent alcohol content defined by the composite disk 12, but also for determining the actual alcohol content when a breath sample is present in the chamber. With the instrument 10, proper stabilization and calibration can thus be verified and an accurate determination of breath alcohol can be made.

When, a switch 68 is switched on, the computer 56 initiates the calibration mode of operation (see FIG. 1). The drive means 50 for the filter wheel 48 is activated and may include a stepper motor (or servo motor) that is synchronized over line 80 with the operation of the computer 56. Thus, the appearance of the filters 53, 55 at designated times assures that the signals representing the two wavelengths can be processed and compared to their respective baseline values in an efficient manner in the computer. The appropriate reading appears at the digital display 62 (that is, either the calibration check value or the sample of ethanol value in the cell 14).

In summary, a calibration device in the form of a composite disk 12, a related method and an apparatus, in the form of a breath analyzing instrument 10, is provided by the present invention that gives improved results and decided advantages over what was available in the prior art. The calibration check is performed by the composite disk 12 in a manner that is not only greatly simplified, but provides a calibration check for accuracy that could only be obtained by more complicated systems, such as the prior art "wet" system. By use of the composite disk 12, the bulky tank is no longer needed, which is of particular importance in mobile installations. Furthermore, the disk 12 which is formed of a silicon substrate 76 and thin coatings 78 of silicon monoxide is rugged in construction and proven to be stable in use over time. Furthermore, a robotic handler including the oscillatable mounting arm 66 and the stepper motor 64 are operative to place the disk 12 into the IR path 42 without the need for manual intervention so that the coatings 78 are protected from attenuation modifying smudges and scratches that have been a problem in the past. The use of the composite disk 12 also enhances the method of calibration described, and improves the instrument 10 for calibration/breath sample analysis, as described.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as is suited to the particular use contemplated. All such modifications and variations are within the scope of the invention as determined by the appended claims when interpreted in accordance with breadth to which they are fairly, legally and equitably entitled.

What is claimed is:

1. A calibration device for a breath alcohol measuring instrument wherein alcohol content in a breath sample is calculated by measuring attenuation of infrared radiation along a radiation path comprising:
   a disk substrate;
   an anti-reflective coating on said substrate, the composition of said disk substrate and said coating attenuating the infrared radiation to provide simulation of a breath sample containing a known percent of alcohol.

2. The device as set forth in claim 1 wherein the composition of said substrate and said coating strongly attenuates infrared radiation at a wavelength of 3.48 microns to simulate a breath sample containing 0.10 percent breath alcohol.

3. The device as set forth in claim 2 wherein:
   said disk substrate includes an approximately 2.5 mm thick silicon disk;
   said anti-reflective coating comprises an approximately 5940 Å thick silicon monoxide coating on both sides.

4. A method for calibration check of a breath alcohol measuring instrument having an infrared radiation source for emitting an infrared beam defining a radiation path to a receiver, a sample chamber along the path, and a computer, the method comprising the steps of:
   providing a substrate with an anti-reflective coating for attenuating the beam;
   storing a known alcohol content value characteristic of the substrate in the computer upon initial setup or calibration of the instrument;
   passing the infrared beam through the substrate and anti-reflective coating for attenuating the infrared radiation of a wavelength of approximately 3.35–3.80 microns to simulate a breath sample with the known alcohol content;
   receiving the attenuated radiation at said receiver;
   computing the simulated value of alcohol concentration from the attenuation of the beam at the receiver; and
   comparing the simulated value to the known alcohol concentration value to check proper calibration of the instrument.

5. The method as set forth in claim 4 wherein said receiving step further includes receiving only infrared radiation of a wavelength of approximately 3.48 microns that is strongly attenuated by breath alcohol.

6. A breath alcohol measuring instrument comprising:
   a sealed sample chamber;
   means for retaining a breath sample in said chamber;
   means for purging with fresh air said sample from said chamber;
   an infrared radiation source and receiver and a radiation path defined therebetween including within said chamber;
   means for filtering the infrared radiation beam so that only infrared radiation of at least one specific wavelength is received at said receiver, the radiation of said wavelength being strongly attenuated by breath alcohol;
   a composite disk for positioning in said path including a substrate coated with an anti-reflective coating for simulating a breath sample with a known alcohol content by causing attenuation of the infrared radiation at said wavelength; and
   computer means for storing a known alcohol content value of the disk upon initial set-up or calibration of the instrument and for determining the simulated attenuation as provided by passing the beam through said disk;
   said computer means being further operative for comparing the known attenuation to said simulated attenuation to check the calibration and for determining actual alcohol content when a breath sample is present in said chamber;
   whereby the proper calibration of said instrument can be verified and an accurate determination of breath alcohol can be made by said instrument.

7. The instrument as set forth in claim 6 further including means for positioning said composite disk into and out of said path for checking the calibration comprising:
   a stepper motor having output shaft; and
   a mounting arm carrying said disk and operatively connected to the output shaft of said stepper motor so that upon activation of said stepper motor by said computer said disk is oscillated into said radiation path.

8. The instrument as set forth in claim 6 wherein said means for filtering includes a first filtering means for filtering out of said radiation beam all wavelengths except at approximately 3.48 microns, which wavelength is strongly attenuated by passing through said disk.

9. The instrument as set forth in claim 8 wherein said means for filtering includes a second filtering means operative for all wavelengths except at approximately 3.8 microns, which wavelength is not attenuated by said disk;

means to alternately introduce said first and second filtering means into said path;

whereby the alternate radiation values are determined for comparison by said computer.

10. The instrument as set forth in claim 9, wherein is provided a wheel for supporting said first and second filtering means;

means for rotating said filter wheel to alternately introduce said filtering means into said path.

11. The instrument as set forth in claim 6 wherein said composite disk includes:

an approximately 2.5 mm thick silicon substrate; and
an approximately 5940 Å thick silicon monoxide coating on both sides of said silicon wafer.

* * * * *